United States Patent [19]

Lin et al.

[11] 4,281,065

[45] Jul. 28, 1981

[54] PHENCYCLIDINE CONJUGATES TO ANTIGENIC PROTEINS AND ENZYMES

[75] Inventors: Cheng-I Lin, San Jose; Prithipal Singh, Santa Clara, both of Calif.

[73] Assignee: Syva Company, Palo Alto, Calif.

[21] Appl. No.: 6,935

[22] Filed: Jan. 25, 1979

[51] Int. Cl.³ .................. C12N 9/96; G01N 33/54; C07G 7/00
[52] U.S. Cl. .................................... 435/188; 435/7; 435/177; 435/190; 260/121; 424/12; 23/230 B
[58] Field of Search ............... 435/7, 174, 177, 188, 435/190; 260/112 R, 121; 424/12, 85, 88; 23/230 B

[56] References Cited

U.S. PATENT DOCUMENTS

| | | | |
|---|---|---|---|
| 3,878,187 | 4/1975 | Schneider et al. | 435/7 |
| 3,966,556 | 6/1976 | Rubenstein et al. | 435/7 |
| 4,065,354 | 12/1977 | Ullman et al. | 435/188 |
| 4,067,959 | 1/1978 | Bolz | 435/7 |

OTHER PUBLICATIONS

Kalir et al., "The Use of Antiaminophencyclidine Antibodies for Development of a Sensitive Radioimmunoassay," *Chem. Abstracts,* vol. 85, No. 21, p. 5 (1976), Abs. #153656y.

*Primary Examiner*—Thomas G. Wiseman
*Attorney, Agent, or Firm*—Bertram I. Rowland

[57] ABSTRACT

Phencylidine, PCP, derivatives having a non-oxo carbonyl functionality linked directly or through a linking group to the phenyl ring are provided for conjugation to antigenic compositions, particularly poly(amino acids), and enzymes. The antigenic conjugates are employed for the production of antibodies, which find particular use in immunoassays for the determination of phencyclidine, while the enzyme conjugate finds use in a homogeneous enzyme immunoassay for the determination of phencyclidine.

10 Claims, No Drawings

PHENCYCLIDINE CONJUGATES TO ANTIGENIC PROTEINS AND ENZYMES

BACKGROUND OF THE INVENTION

1. Field of the Invention 1-(1'-phenylcyclohexyl-1')piperidine, otherwise known as phencyclidine, PCP, was originally used as an analgesic anaesthetic drug (pain-killing) for humans. It is now legally used exclusively as an animal tranquilizer due to its strong side effects, such as euphoria and hallucinations. Probably because of these side effects, PCP has become prevalent in the illicit drug market. It is often sold as "peace pill", "angel dust", "dust", "crystal", or "supergrass".

PCP is a dangerous and potent drug with lethal potential and has become a major drug abuse problem. Thus it is desirable that there be a simple accurate rapid technique for detecting the presence of PCP in physiological fluids, such as blood serum, urine and saliva.

2. Description of the Prior Art

There have been difficulties in attempting to identify PCP in physiological fluids. In one investigation (D. C. K. Lin et al., *Biochem. Mass Spec.* 206 (1975)) of urine from patients intoxicated by PCP, no metabolites were detected in untreated urine. However, two urinary metabolites were freed from conjugates by enzymatic hydrolysis and identified as 4-phenyl-4-piperidinocyclohexanol and 1-(1-phenylcyclohexyl)-4-hydroxypiperidine. An additional metabolite, tentatively identified as 1-phenyl-(4-hydroxycarboxyl)-4-hydroxypiperidine, was found in the urine from rhesus monkeys after administration of PCP.

DESCRIPTION OF THE SPECIFIC EMBODIMENTS

Phencyclidine, PCP, derivatives are provided having a non-oxo carbonyl functionality (including the nitrogen and sulfur analogs thereof) linked directly or through a linking group to the phenyl ring for conjugation to poly(amino acids), which are antigenic or enzymes. The antigenic conjugates are employed for the production of antibodies which are specific for phencyclidine, the antibodies finding use in immunoassays. The enzyme conjugates are employed as reagents in homogeneous enzyme immunoassays for the determination of phencyclidine.

The phencyclidine precursors employed for conjugation to poly(amino acids) will have from about 18 to 30 carbon atoms, usually 18 to 28 carbon atoms and preferably 20 to 24, having in addition to the nitrogen of the phencyclidyl from 2 to 8, usually 2 to 6, and preferably 2 to 4 heteroatoms which are chalcogen (O and S) or nitrogen, preferably oxygen. The preferred linking functionality is non-oxo carbonyl (including the nitrogen and sulfur analogs thereof) and the linking group is usually bonded to the phenyl ring, at least 3 carbon atoms from the attachment to the cyclohexyl ring, i.e. meta or para. Any oxygen is present as carbonyl, oxo or non-oxo, or oxy, sulfur is present as thiono or thio and nitrogen is present as amino bonded solely to carbon or amido.

For the most part, the compounds of this invention will have the following formula:

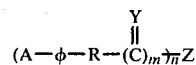

wherein:

A is 1-(N-piperidyl)cyclohexyl-1;

$\phi$ is phenylene, usually other than ortho, preferably para;

R is a linking group which is a bond or divalent aliphatic group, hydrocarbon or non-hydrocarbon, of from 1 to 10 atoms other than H, which are generally C, N or chalcogen, e.g. O and S, having from 1 to 8, usually 1 to 6, preferably 2 to 6 carbon atoms and having from 0 to 4, preferably 0 to 2 heteroatoms which are bonded solely to C and H, wherein O and S are oxo or oxy or the S analogs, e.g. thiono or thio, preferably oxy, and are bonded solely to aliphatically saturated carbon (includes aromatic carbon) and N is bonded solely to C or is amido; R may have 0 to 1 site of aliphatic unsaturation, e.g. ethylenic, with the proviso that when m is 0, R terminates in a methylene group;

Y is chalogen, e.g. S or O, or NH and is preferably O;

Z is hydrogen, hydroxyl, alkoxyl of from 1 to 6 carbon atoms, an activating oxy group to form an activated ester capable of amide formation in an aqueous medium, e.g. N-oxy succinimide and p-nitrophenoxy, or a poly(amino acid), which is antigenic or an enzyme, which poly(amino acid) is joined by a bond to a methylene group when m is 0 and by an amide bond when m is one;

m is 0 or 1 when Z is a poly(amino acid) and is otherwise one;

n is 1 when Z is other than a poly(amino acid) and is otherwise 1 to the molecular weight of Z divided by 500, more usually divided by 1000, and frequently divided by 1500, generally ranging from 1 to 500, preferably from 10 to 100, when Z is an antigen, and from 1 to 30, more usually from 2 to 20, and preferably from 2 to 16, when Z is an enzyme.

Preferred R groups include alkylenes, such as ethylene, propylene, butylene, pentylene, hexylene, heptylene, octylene, 2-methylpropylene, etc.; alkenylenes such as 2-butenylene, 2-pentenylene, vinylene, etc.; and oxyalkylenes and oxyalkenylenes such as ethyleneoxymethylene, ethyleneoxyethylene, 1-methyleneoxy-2-propenylene, heptyleneoxyethylene, etc.

For those compounds where n is one, the compounds will have the formula:

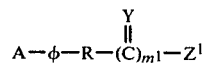

wherein

A, $\phi$, R and Y have been defined previously, $m^1$ is one, and $Z^1$ is hydrogen, alkoxyl of from 1 to 6, more usually from 1 to 3 carbon atoms, particularly methyl and ethyl, an oxy group forming an activated ester which readily reacts with the amine group of poly(amino acids) under mild conditions in an aqueous medium to form amides, such as N-oxy succinimide or p-nitrophenyl, or is hydroxyl.

Where n is at least 1 and Z is a poly(amino acid), the compounds will for the most part have the following formula:

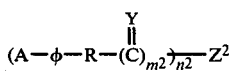

wherein

A, φ, R and Y have been defined previously;
$Z^2$ is a poly(amino acid) which is either antigenic or an enzyme;
$m^2$ is 0 or 1, preferably 1; and
$n^2$ is at least 1, and usually greater than 1;
when $Z^2$ is antigenic, $n^2$ will normally be at least 2, and not greater than the molecular weight of $Z^2$ divided by 500, usually not greater than the molecular weight of $Z^2$ divided by 1000, and preferably not greater than the molecular weight of $Z^2$ divided by 1500, generally ranging from 2 to 500; when $Z^2$ is an enzyme, $n^2$ will be at least 1, usually not greater than 30, more usually in the range of 2 to 20, and preferably in the range of about 2 to 16.

The poly(amino acids) will generally range from about 5,000 molecular weight, having no upper molecular weight limit, normally being less than 10,000,000 usually not more than about 600,000. There will usually be different ranges, depending on whether an antigen or an enzyme is involved, with antigens ranging from about 5,000 to $10^7$, usually from about 20,000 to 600,000 and more usually from about 25,000 to 250,000 molecular weight; while enzymes will generally range from about 10,000 to 600,000, more usually from about 10,000 to 300,000 molecular weight. There will usually be at least about one conjugate per 500,000 molecular weight, more usually at least one per 50,000 molecular weight. With intermediate molecular weight antigens (35,000 to 1,000,000), the number of conjugate groups will generally be from about 2 to 250, more usually from 10 to 100. With lower molecular weight antigens, below 35,000, the number of conjugates will generally be in the range of from about 2 to 10, usually in the range of 2 to 5.

Various protein types may be employed as the antigenic material. These types include albumins, serum proteins, e.g., globulins, ocular lens proteins, lipoproteins, etc. Illustrative proteins include bovine serum albumin, keyhole limpet hemocyanin, egg ovalbumin, bovine γ-globulin, etc. Alternatively, synthetic poly(amino acids) may be prepared having a sufficient number of available amino groups, e.g., lysines.

The enzymes can be varied widely, depending upon the rapidity with which one desires a result and the physiological fluid in which the phencyclidine is to be measured. Finally, the enzymes of choice, based on the I.U.B. classification are: Class 1. Oxidoreductases and Class 3. Hydrolases. Particularly in Class 1, the enzymes of interest are dehydrogenases of Class 1.1, more particularly 1.1.1 and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the peroxidases, horse radish peroxidase is illustrative. Of the hydrolases, alkaline phosphatase, β-galactosidase, β-glucosidase and lysozyme are illustrative.

Particularly preferred are those enzymes which employ nicotinamide adenine dinucleotide (NAD) or its phosphate (NADP) as a cofactor, particularly the former. Most preferred as the choice of enzyme is glucose 6-phosphate dehydrogenase.

The preferred enzymes will retain at least about 40%, preferably at least about 60% of their original activity after conjugation, and will be inhibited when saturated with antibody to the hapten at least about 40%, preferably at least about 60% and not more than 99%, preferably not more than about 95%.

The synthetic scheme for preparing the subject compounds is set forth in the following flowchart:

CHART 1

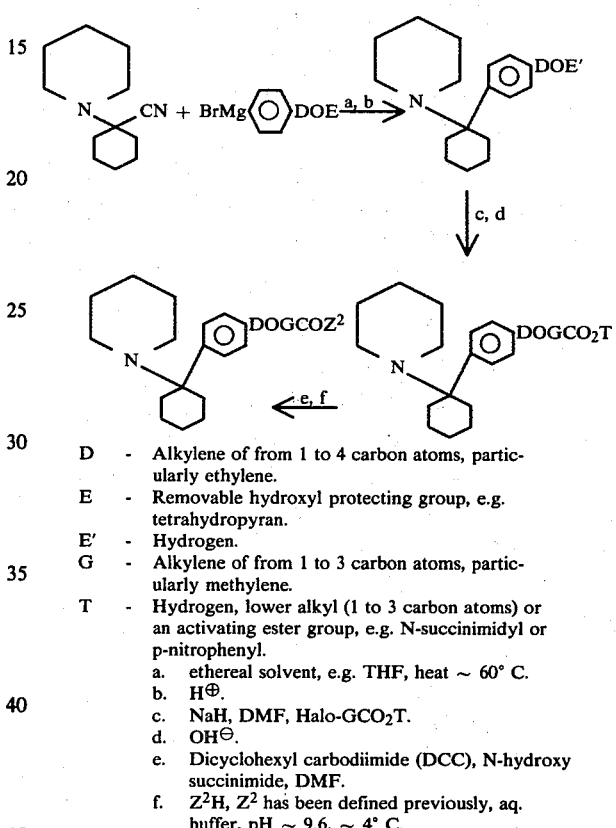

D - Alkylene of from 1 to 4 carbon atoms, particularly ethylene.
E - Removable hydroxyl protecting group, e.g. tetrahydropyran.
E' - Hydrogen.
G - Alkylene of from 1 to 3 carbon atoms, particularly methylene.
T - Hydrogen, lower alkyl (1 to 3 carbon atoms) or an activating ester group, e.g. N-succinimidyl or p-nitrophenyl.
  a. ethereal solvent, e.g. THF, heat ~ 60° C.
  b. H⊕.
  c. NaH, DMF, Halo-GCO$_2$T.
  d. OH⊖.
  e. Dicyclohexyl carbodiimide (DCC), N-hydroxy succinimide, DMF.
  f. $Z^2$H, $Z^2$ has been defined previously, aq. buffer, pH ~ 9.6, ~ 4° C.

In carrying out the preparation of the compositions of this invention, 1-(1'-cyanocyclohexyl)piperidine is first prepared by the reaction of cyclohexanone, piperidine and potassium cyanide in the presence of concentrated HCl, and added in an anhydrous inert ethereal solvent to a stirring solution of phenylalkanol ether Grignard reagent at room temperature to provide an Ar substituted derivative of phencyclidine. The PCP-alcohol thus prepared, is substituted with a haloaliphatic carboxylic acid alkylester ether linkage and the ester hydrolyzed. The carboxylic acid may then be employed to form an activated ester which reacts in an aqueous medium with amino groups of poly(amino acids) to form amide bonds. The ester may be formed for example by employing a carbodiimide to activate the carboxylic acid. The resulting ester may then be combined with the appropriate poly(amino acid) in an aqueous buffered medium at moderate temperature and the pH maintained and monitored during the addition of the ester to the poly(amino acid).

By employing the above procedure, the phencyclidine is functionalized to a compound which can be conjugated to poly(amino acids) either antigenic or enzymes. The structure of the PCP is retained during the synthetic procedure and those elements of the structure which provide for distinctions between closely similar compounds are exposed to allow for formation of antibodies which are capable of distinguishing PCP from similarly structured compounds. The antigenic conjugates may be injected into a wide variety of vertebrates in accordance with conventional methods for the production of antibodies. Usually the animals are bled periodically with successive bleeds having improved titer and specificity and then plateauing and diminishing in their specificity and titer.

As previously indicated, the antibodies and enzyme reagents prepared in accordance with the subject invention find particular use in immunoassays for the determination of PCP. A description of the method for carrying out the immunoassay, which is a homogeneous enzyme immunoassay, may be found in U.S. Pat. No. 3,817,837. The method involves combining the enzyme conjugate, the unknown sample suspected of containing PCP, and an antibody for PCP in an aqueous buffered medium at temperatures in the range of about 10° to 50° C., more usually from about 20° to 40° C., and determining the enzyme activity as compared to the enzyme activity of an assay medium having a known amount of PCP.

EXPERIMENTAL

Ex. 1. Preparation of 1-Piperidinocyclohexanecarbonitrile

Piperidine (44 g, 0.52 mole) was carefully mixed with 45 ml of concentrated HCl and 120 ml of cold water (pH ~3-4). To this solution, 50 g (0.52 mole) of cyclohexanone was added, followed by 36 g of KCN in 100 ml of water with vigorous stirring.

The resulting solution was allowed to stir at room temperature overnight. (After 2 hours, a white precipitate was formed.) The crystalline precipitate was collected by filtration, washed with cold water, and then recrystallized from 95% ethanol (300 ml) to yield 1-piperidinocyclohexanecarbonitrile (88 g) as a crystalline solid mp. 66°–68°.

Ex. 2. Preparation of THP of p-Bromophenethyl Alcohol p-Bromophenethyl alcohol (Aldrich, 10.5 g, 0.05 mole) was added to a stirring solution of 10 g (0.12 mole) dihydropyran in 100 ml of ethyl ether containing a few crystals of p-tolylsulfonic acid.

The solution was stirred at room temperature for one hour and then 10 ml of 0.1 N sodium hydroxide was added to it. The aqueous solution was separated and the ethereal solution was dried over sodium sulfate, concentrated and vacuum distilled yielding 12.4 g of clear liquid product (87% yield).

Ex. 3. Preparation of 1-(1'-Phenylcyclohexyl-1')piperidine Alcoholic Derivative

Tetrahydropyran protected p-bromophenethyl alcohol prepared in Example 2 (8 g, 0.028 mole) was dissolved in 150 ml of freshly distilled anhydrous THF in a 500 ml flask under argon. To this solution, magnesium (1.2 g, washed with dil. HCl, acetone, ether and dried) was added, followed by a few pieces of iodine and a few drops of dibromoethane.

As soon as there was gas evolution, the solution was heated to ~60° with stirring. The mixture continued to be stirred at 60° for 4 hours under argon. After cooling to room temperature, a solution of 5.4 g (0.028 mole) 1-piperidinecyclohexanecarbonitrile prepared in Example 1 in 50 ml of anhydrous THF was slowly added with vigorous stirring. After complete addition, the solution was allowed to stir at room temperature overnight.

Saturated ammonium chloride (50 ml) was added followed by 200 ml of ethyl ether. The organic solution was separated and was dried over sodium sulfate. Solvent was removed under reduced pressure to give a brown liquid as product.

The crude product was dissolved in 200 ml of ether and was extracted with 3×60 ml of 20% HCl solution. The combined aqueous solutions were extracted with 2×100 ml of ethyl ether. The aqueous solution was then adjusted to pH~8 with ammonium hydroxide and was extracted with 5×100 ml of ethyl ether. The ethereal solution was dried over sodium sulfate and was concentrated under reduced pressure to give 6.5 g (88% yield) of desired product as a heavy oil.

Ex. 4. Preparation of Ester of PCP-Alcoholic Derivative

A solution of PCP-alcoholic derivative prepared in Example 3 (6.1 g, 0.021 mole) in 35 ml of anhydrous DMF (distilled over $CaH_2$) was added to a suspended sodium hydride (50% oil dispersion, 1.44 g, 0.03 mole, washed with 3×10 ml of petroleum ether) solution (60 ml of anhydrous DMF) under argon atmosphere.

The solution was heated to ~55° for 2 hours and then cooled to room temperature. Ethyl bromoacetate (5 g, 0.03 mole) in 40 ml of DMF was then added dropwise. After complete addition, the solution was allowed to stir at room temperature overnight.

After a small amount of water was added, the solution was concentrated to dryness in vacuo. The residue was taken up with chloroform.

The chloroform solution was chromatographed on silica gel thin layer plates (20% methanol/chloroform) to give 1.45 g of the desired ester (1 of 3 spots on tlc, Rf 0.89, 18.5% yield).

Ex. 5. Hydrolysis of PCP-Ester

PCP-ester prepared in Example 4 (1.43 g, 3.8 mmole) was dissolved in 40 ml of methanol and was added to 10 ml of 1 N sodium hydroxide solution. The mixture was allowed to stir at room temperature for 4 hours.

The solution was concentrated to dryness in vacuo and the residue was dissolved in 20 ml of water.

The aqueous solution was adjusted to pH~6 by treatment with acetic acid. The solution was then concentrated to dryness in vacuo. The solid residue was extracted with chloroform several times. The combined organic solution was concentrated and the residue was chromatographed on a silica gel plate with a 20% methanol chloroform solution (saturated with anhydrous ammonia) as eluent (Rf 0.3) to give 1.1 g of the corresponding acid (83% yield) mp. 198°–200° C.

Ex. 6. Conjugation of PCP-Acid to BSA

1. Preparation of Activated NHS-Ester

PCP-acid (150 mg, $4.35 \times 10^{-4}$ mole), NHS (65 mg, $5.65 \times 10^{-4}$ mole) and dicyclohexyl carbodiimide (DCC) (112 mg, $5.49 \times 10^{-4}$ mole) were placed in a 5 ml flask. The flask was connected to a vacuum for 30 minutes and 4 ml of DMF (dried and distilled over CaH$_2$) was then added under an argon atmosphere. The solution (heterogeneous) was allowed to stir at room temperature for 40 hours.

2. Preparation of BSA Solution

BSA (500 mg) was dissolved in 40 ml of sodium bicarbonate-sodium carbonate buffer (both 0.1 N, pH 9.6 at 20° C.) at ice-bath temperature.

The activatived NHS-ester solution was slowly added to the stirring protein solution through a glass-wool-packed pipet. After completion, the pipet was washed with 1 ml of DMF. The solution was then stirred in the cold room for 40 hours before dialysis.

3. Purification

The conjugated protein solution was transferred to a membrane tubing and was dialyzed against 4×4 liter of water at pH~9.5 (3-4 hours at each interval). After dialysis, the solution was passed through 250 ml of G-50 Sephadex column followed by filtering through 0.22 μm millipore membrane. The solution was lyophilized to yield 503 mg protein (hapten number 20 by UV).

Ex. 7. Conjugation of PCP-Acid to BgG

PCP-acid (150 mg, $4.35 \times 10^{-4}$ mole), NHS (65 mg, $5.65 \times 10^{-4}$ mole) and DCC (95 mg, $4.61 \times 10^{-4}$ mole) were placed in a 5 ml flask. The mixture was dried in vacuo for 30 minutes. Chloroform (2 ml, freshly distilled over CaCl$_2$) and THF (2 ml, distilled over LAH) were added with stirring at ice-bath temperature under argon atmosphere. The solution was allowed to stir at ~4° overnight.

The solution was concentrated in vacuo to dryness and the residue was slowly transferred into a stirring BgG solution by 1 ml of THF. The flask was then rinsed with 10 ml of sodium bicarbonate/sodium carbonate buffer solution and was added to the protein solution.

BgG solution was prepared by dissolving 550 mg of BgG in 80 ml of sodium bicarbonate/sodium carbonate (0.1 N, pH 9.6) buffer solution at ice-bath temperature.

The conjugated protein solution was allowed to stir in the cold-room overnight, and then was transferred to membrane tubing for dialysis. After dialyzing against water (5×4 liter, pH~9.5), the solution was centrifuged at $10^3$ rpm to spin down unwanted precipitate. The supernatant was lyophilized to yield protein of hapten number 37 (determined by TNBS).

Ex. 8. Conjugation of PCP-Acid to Glucose-6-Phosphate Dehydrogenase (G-6-PDH)

Before employing the reactants, the reactants were dried over P$_2$O$_5$ at 0.5 mmHg for 15 hrs. Into a dry reaction flask was introduced 2 ml dry DMF and 34.5 mg (0.1 mmoles) of PCP-acid (Ex. 5) while maintaining the flask dry with a serum stopper and drying tube. To the agitated slurry was added 12.65 mg (0.11 mmole) of N-hydroxy succinimide and 21.12 mg (0.11 mmoles) of EDAC (ethyl 3-dimethylaminopropyl carbodiimide and the mixture stirred for about three days at room temperature to obtain a clear yellow ~0.05 M solution.

The enzyme solution was diluted in tris-HCl buffer (0.05 M, pH 8.1) to 2.5-3.0 mg/ml and 5 ml added to a reaction flask. To the solution is added with stirring G6P(Na$_2$) and NADH to concentrations of 20 mg/ml and 30 mg/ml respectively, followed by 1.5 ml of carbitol, which is slowly added over a period of 5-10 min. The pH is monitored being maintained in the range 8.5-9.0 with 1 N aq. NaOH. The ester solution is then added at a rate of about 1-2 μl/min and the enzyme parameters monitored until about 17-20% deactivation and 63-68% inhibition is obtained when a saturating amount of anti(phencyclidine) is added to the conjugated enzyme. A total of 100 μl of hapten was added to 19.9% deactivation, 65.7% inhibition. The protocol will be described below.

The crude enzyme conjugate is purified by chromatographing on a Sephadex G-50 column and eluting with tris-HCl (0.055 M, pH 8.0) and fractions showing a ΔOD of 300 or greater collected and pooled.

In order to demonstrate the efficacy of compounds prepared in accordance with the subject invention, the antibodies and the enzyme conjugate were employed in a number of assays for phencyclidine.

The enzyme is assayed as follows. The following reagents are employed:

Buffer:
  0.055 M tris-HCl pH 8.1 (RT)
Enzyme conjugate:
  Buffer
  0.9% NaCl
  1.0% RSA, pH 8.1 (RT)
  Sufficient enzyme conjugate to give a maximum rate of ΔOD equal to 600-900 in the assay medium
Assay Buffer:
  Buffer
  0.5% NaCl
  0.01% v/v Triton X-100, pH 8.1 (RT)
Antibody Reagent:
  Buffer
  1.0% RSA
  G6P(Na$_2$) 0.066 M
  NAD 0.04 M, pH 5 RT
  Antiphencylidine optimized for assay (All % indicated are w/v g/ml. RSA—rabbit serum albumin. G6P-glucose-6-phosphate. NAD—nicotinamide adenine dinucleotide.)

The protocol employed is to dilute 50 μl of the sample with 250 μl of the assay buffer, and take a 50 μl aliquot and dilute this aliquot with 250 μl of assay buffer, followed by 50 μl of the antibody reagent diluted with 250 μl of assay buffer, followed by 50 μl of enzyme reagent diluted with 250 μl of assay buffer. After addition of the enzyme reagent, the solution is aspirated into a flow cell of a Gilford 300 N microsample spectrophotometer equipped with a thermocuvette and readings made at 340 nm at 10 sec and 40 seconds from time of introduction. The results are reported as the difference in absorbance (ΔOD)×2.667.

To demonstrate the sensitivity of the assay, samples having varying amounts of phencyclidine were prepared and assayed. The following table indicates the results.

| Phencyclidine ng/ml | ΔOD |
|---|---|
| 0 | 268 |
| 25 | 306 |
| 100 | 377 |

The above results demonstrate that a sensitive response to small changes in phencyclidine concentration can be achieved over the concentration range of interest. Thus, an assay is provided which is rapid, simple, accurate and sensitive, providing for the specific determination of phencyclidine.

The synthetic procedure provides for the preparation of phencyclidine derivatives without substantial modification of the structure which would have resulted in loss of specificity of the antibodies and the enzyme reagent. Thus, a synthetic route is provided to produce antibodies which are specific for phencyclidine.

Although the foregoing invention has been described in some detail by way of illustration and example for purposes of clarity and understanding it will be obvious that certain changes and modifications may be practiced within the scope of the appended claims.

What is claimed is:

1. Compound of the formula:

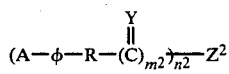

wherein:
A is 1-(N piperidyl)cyclohexyl-1;
$\phi$ is p-phenylene;
R is a divalent aliphatic group of from 2 to 6 carbon atoms and 0 to 1 oxygen atom bonded solely to aliphatically saturated carbon atoms;
Y is oxygen;
$m^2$ is one;
$Z^2$ is a poly(amino acid);
$n^2$ is at least one and not greater than the molecular weight of $Z^2$ divided by 500.

2. Compound according to claim 1, wherein $Z^2$ is an enzyme, and $n^2$ is in the range of 2 to 16.

3. Compound according to claim 2, wherein said enzyme is glucose-6-phosphate dehydrogenase.

4. Compound according to claim 1, wherein $Z^2$ is an antigen, and $n^2$ is in the range of about 2 to 500.

5. Compound according to claim 4, wherein said antigen is globulin.

6. Compound according to claim 4 wherein said antigen is an albumin.

7. Conjugate of 5-(4'-(1''-(N-piperidino)cyclohexyl-1'')phenyl-1')-3-oxapentanoic acid with glucose-6-phosphate dehydrogenase connected by amide bonds.

8. Conjugate of 5-(4'-(1''-(N-piperidino)cyclohexyl-1'')phenyl-1')-3-oxapentanoic acid with a poly(amino acid) antigen connected by amide bonds.

9. Conjugate according to claim 8, wherein said antigen is a globulin.

10. Conjugate according to claim 8, wherein said antigen is an albumin.

* * * * *